(12) United States Patent
Doss

(10) Patent No.: US 7,700,079 B2
(45) Date of Patent: *Apr. 20, 2010

(54) THERAPEUTIC SOAP PRODUCT WITH UV PROTECTION

(76) Inventor: Jamie Collins Doss, 211 Rosario Blvd., Condo 11, Santa Fe, NM (US) 87501

( * ) Notice: Subject to any disclaimer, the term of this patent is extended or adjusted under 35 U.S.C. 154(b) by 777 days.

This patent is subject to a terminal disclaimer.

(21) Appl. No.: 11/234,097

(22) Filed: Sep. 26, 2005

(65) Prior Publication Data

US 2007/0071698 A1    Mar. 29, 2007

(51) Int. Cl.
- *A61K 8/00* (2006.01)
- *A61K 31/74* (2006.01)
- *A61K 8/02* (2006.01)
- *A61K 36/328* (2006.01)
- *A61Q 5/00* (2006.01)

(52) U.S. Cl. .............. 424/59; 424/70.9; 424/78.05; 424/401; 424/748

(58) Field of Classification Search .............. 424/59, 424/60, 400, 401, 70.9, 78.05, 748
See application file for complete search history.

(56) References Cited

U.S. PATENT DOCUMENTS

| | | | |
|---|---|---|---|
| 4,701,321 A | 10/1987 | Bernstein | |
| 4,707,354 A * | 11/1987 | Garlen et al. | 424/47 |
| 4,933,174 A | 6/1990 | Bernstein | |
| 5,182,103 A | 1/1993 | Nakane et al. | |
| 5,223,244 A | 6/1993 | Moro et al. | |
| 5,340,567 A * | 8/1994 | Cole et al. | 424/59 |
| 5,462,736 A | 10/1995 | Rech et al. | |
| 5,538,740 A | 7/1996 | Abad | |
| 5,614,197 A | 3/1997 | Pathak et al. | |
| 5,650,137 A | 7/1997 | Nguyen et al. | |
| 5,747,049 A | 5/1998 | Tominaga | |
| 5,762,915 A | 6/1998 | Saito et al. | |
| 5,830,486 A | 11/1998 | Namba et al. | |
| 5,853,705 A | 12/1998 | Nakayama et al. | |
| 5,948,393 A | 9/1999 | Tomomasa et al. | |
| 6,034,204 A | 3/2000 | Mohr et al. | |
| 6,036,946 A | 3/2000 | Greene | |
| 6,077,520 A | 6/2000 | Tominaga | |
| 6,174,519 B1 | 1/2001 | Greene | |
| 6,217,852 B1 | 4/2001 | Gildenberg et al. | |
| 6,235,272 B1 | 5/2001 | Greene | |
| 6,294,186 B1 | 9/2001 | Beerse et al. | |
| 6,423,329 B1 * | 7/2002 | Sine et al. | 424/405 |
| 6,607,736 B2 | 8/2003 | Ohmori et al. | |
| 6,749,838 B1 | 6/2004 | Joichi et al. | |
| 6,770,270 B2 | 8/2004 | Bonda | |
| 6,787,147 B1 * | 9/2004 | Huner et al. | 424/401 |
| 6,811,769 B2 | 11/2004 | Watanabe | |
| 7,001,592 B1 * | 2/2006 | Traynor et al. | 424/59 |
| 2005/0124705 A1 * | 6/2005 | Schreiber et al. | 516/53 |
| 2006/0134238 A1 * | 6/2006 | Dnyaneshwar | 424/744 |

OTHER PUBLICATIONS

U.S. Appl. No. 11/234,096, filed Sep. 2005, Doss, J. C.*

* cited by examiner

Primary Examiner—Johann R Richter
Assistant Examiner—Mei-Ping Chui
(74) Attorney, Agent, or Firm—John J. Yim

(57) ABSTRACT

The present invention concerns a cleansing composition that imparts sun protection for the skin through normal daily use during bathing, washing, or cleaning of the body or face. The cleansing composition of the present invention comprises a unique combination of ingredients that provides therapeutic and restorative properties for the skin.

11 Claims, No Drawings

THERAPEUTIC SOAP PRODUCT WITH UV PROTECTION

CROSS REFERENCE TO RELATED APPLICATION

This patent application is related to a concurrently filed utility patent application entitled "Therapeutic Soap Product with UV Protection," filed on Sep. 9, 2005, and assigned Ser. No. 11/234,096. The concurrently filed application is incorporated herein by reference.

INTRODUCTION

The sun is vital and necessary for almost all forms of life. But it is well documented that overexposure to the sun's ultraviolet ("UV") rays harms the skin. The sun's UV rays damage the skin and cause premature aging and sunburns. It is the primary cause of skin cancer. New incidences of skin cancer are estimated to exceed 1.3 million cases each year. Two new cases of skin cancer are diagnosed every minute, and one person dies of skin cancer every hour.

Despite these known dangers, however, most people do not take the necessary precautions to protect themselves from overexposure to the sun. Surveys have found that one in seven adults do nothing to protect themselves from the sun. When asked why, one in three adults answered that they simply forgot.

Solar UV radiation causes damage to cell membranes and the DNA molecules inside the cells. It also helps break down collagen fibers and elastin, which are proteins that are vitally important for maintaining the skin's structural integrity. UV radiation causes collagen to break down faster than with the normal aging process. Repeated overexposure to the sun causes a thickening of the skin that produces a tough, leathery skin and unsightly changes in skin pigmentation. Overexposure to the sun and its UV rays cosmetically harms the skin, causing freckles, wrinkles, premature skin aging, solar lentago, solar elastosis, and pigment coloration changes, among other skin blemishes.

As people increasingly engage in the modern outdoor lifestyle, these health and cosmetic concerns become more urgent. Furthermore, increasing depletion of the ozone layer and increasing pollution continue to exacerbate the sun's harmful effect. UVA rays, which comprise approximately 90-95% of the sun's ultraviolet light, have a relatively long wavelength in the 320-400 nanometer range. UVA rays are not absorbed by the ozone layer and are the primary cause of initial stages of a tan. UVB rays, with medium wavelength of about 290-320 nanometers, are partially absorbed by the ozone layer and are the primary cause of a sunburn.

For health and cosmetic benefits, overexposure to the sun should be avoided, and sunscreen products should be used when going out into the sun. Various sunscreen products have been developed and widely used for protection against UVA and UVB rays. The skin-care market currently sells sunscreen products generally in two different forms: as chemical absorbers or as physical blockers.

Chemical sunscreens contain one or more UV absorbing chemical components such as abovenzone, octocrylene, benzophenones, salicylate, and cinnamates. Although they are effective in shielding the body against the sun's effect, they also cause adverse skin reactions. Some studies have also found that chemical sunscreens generate harmful free radicals and may actually increase the risk of cancer. Some commonly used chemical sunscreens also have strong estrogenic actions that may lead to complications.

In contrast, physical blockers or inorganic sunscreens physically scatter and reflect UVB and UVA rays. Physical sunblocks, such as zinc oxide or titanium dioxide, are not absorbed by the skin and are not known to cause health complications.

In addition to the time consuming nature of proper application, sunscreen products can be difficult to apply over the whole body. Even when applied properly, it must be applied repeatedly and in ample amounts. Additionally, a sunscreen lotion may be uncomfortable for some because of the oily/greasy feel it may leave behind. Thus, there is a need for a product that allows its users to apply sunblock on a daily basis in a convenient and easy manner.

The skin is also the body's largest organ. The epidermis, which is the outermost layer, functions primarily as a protective barrier, while the dermis is the underlying layer. The skin provides the vital function of protecting the body against physical and chemical elements. The blood vessels in the skin also regulate body temperature, and the skin functions as an important sensorial tool. In addition to providing protection and regulating the body, the skin also functions as a shock absorber and an insulator.

No matter the age or skin type, proper skin care also involves proper cleaning, nourishing, moisturizing, and protecting. A good cleanser or soap rids the skin of the dirt and pollutants that accumulate over the course of a day without causing drying or adverse reaction. As an important and active organ, the skin also needs to be nourished with nutrients and moisturizers.

As an active organ, the skin is also susceptible to damages and ailments. Sunburns caused by overexposure should be treated promptly. Likewise, skin conditions such as eczema, acne, irregular pigmentation and the like should also be treated. Thus, there is a need for a skin product that simultaneously provides therapy and maintenance for healthy skin. Thus, there is a need in the art for an improved skin cleansing composition that safely washes and therapeutically treats the skin, while applying sunblock through the normal use of the soap.

The cleansing composition of the present invention applies sunscreen protection to the skin through the normal routine of bathing or washing with a bar of soap. As a result, it can be applied to the whole body and face quite efficiently and better suited for use on a daily basis. The composition is also suited for frequent use because of the non-greasy, all natural, and hypoallergenic formulation. The soap composition of the present invention further comprises ingredients that strengthen and nourish the skin.

For those with fair or sensitive skin, the cleansing composition of the present invention provides additional advantages. The present invention allows those with sensitive skin to wear sunscreen protection without forgetting. Additionally, the present invention does not have harsh or unnatural ingredients and thus makes it appropriate for individuals with sensitive skin.

Another advantage of the present invention is that it is a therapeutic product. A therapeutic product generally heals and nourishes the skin, thereby promoting a healthier skin. Just as one cares for the internal part of the body by eating the right foods and taking vitamins, the soap composition of the present invention also nourishes and cares for the skin by providing various therapeutic ingredients. The unique formulation of the present invention provides manifold advantages:

it gently cleans the skin, it protects the skin against the sun, and it nurtures and heals the skin.

SUMMARY OF INVENTION

The present invention concerns a cleansing composition that applies sunblock to the skin through normal daily use. The cleansing composition is preferably in a soap bar form. In normal use, users will generally wash with the soap bar and rinse off with water in the ordinary course of washing. Despite rinsing off, the composition of the present invention imparts and leaves behind a UV protectant for the skin.

The cleansing composition of the present invention also provides therapeutic benefits to the skin. The present invention comprises a unique combination of ingredients that provides therapeutic and restorative properties for the skin. Repeated use of the composition of the present invention reduces skin ailments and cosmetic blemishes such as acne, freckles, and age spots. The composition is especially useful for those with sensitive and fair skin. The all-natural based formulation leaves no noticeable oil or residues that may cause adverse skin reactions. Because the present invention is also gentle for daily use even by those with the most sensitive skin, it can be used regularly without harm or side effect. The soap composition of the present invention also preferably does not use any non-natural ingredients and preferably does not use allergic ingredients.

The present invention comprises a natural soap base. Preferably, glycerin, a natural humectant, is used as the soap base. Glycerin is hypo-allergenic and safe for use on sensitive skin. Other hypo-allergenic soap bases may also be used as known in the art. For example, the soap base may comprise approximately 15-20% pure glycerin, to which may be added approximately 7-13% additional lipids. Preferably, vegetable or plant derived soap bases are chosen. Olive oil or coconut oil bases may also be used, but lye derived soap bases are preferably avoided.

As UV protectants, the soap bar composition of the present invention comprises physical sunblocks, titanium dioxide and zinc oxide. These physical sunblocks keep UVA and UVB rays from reaching the skin, and they block the UV rays rather than absorbing them like chemical sunscreens.

In preferred embodiments, ultrafine or microfine forms of these physical sunblocks are used. Their small size makes them clear and cosmetically suitable. More preferably, the zinc oxide is in nanospheric form to allow for better blending with the other ingredients of the present invention. Titanium dioxide and zinc oxide also possess therapeutic properties that are beneficial to the skin. Preferably, titanium dioxide and zinc oxide are blended or paired together in making the inventive composition.

In addition to the soap base and the physical UV protectants, the soap composition of the present invention further comprises the following ingredients: chlorophyll, citric acid, the healing balm of Gilead, aloe vera, vitamins, minerals, olive oil, and amino acids.

In adding these ingredients, the liquid to powder ratio is balanced to provide for optimal texture, consistency and hardness of the resulting soap product. For example, the amount of liquid added is adjusted so that the resulting product will have optimal texture, consistency and hardness of a soap bar as known in the art. If too much powder ingredients are used, for example, the soap product may have inappropriate texture, consistency and hardness. Many of the ingredients can be used in either liquid or powder (or solid) forms, and the final consistency, texture and hardness of the soap product should be considered in making the adjustments. As known in the art, different combinations of liquid to powder proportions may be used.

Chlorophyll, for example, may be added in either liquid or powder form. Preferably, chlorophyll is added in liquid form. The chlorophyll used in the present invention is preferably made without additives or preservatives. In some embodiments, chlorophyll may be added in both powder and liquid forms. Chlorophyll promotes skin restoration and skin therapy and provides treatment for burns, sunburns, abrasions and skin irritations. It also gives the soap product of the present invention anti-bacterial and detoxifying properties.

Alpha-hydroxy acids, preferably organic acids, and more preferably citric acids are also added in the inventive compound. These alpha-hydroxy acids are derived from foods, such as milk, wine, fruits and citrus. Citric acids are used at low concentrations, and they help gently exfoliate the skin. It helps remove the outer layer of dead skin cells and thus helps the skin in its natural regenerating process. The citric acid helps the skin achieve and maintain a smoother, fresher, younger-looking skin and increases the skin's thickness. Also functioning as a skin moisturizer, the citric acid improves the overall tone of the skin and reduces lines. Since too much alpha-hydroxy acids may render the skin sensitive, low concentrations are added to the present invention. Furthermore, the sunscreen in the inventive composition further protects the skin from being damaged by the sun.

The present invention also comprises the healing balm of Gilead. The balm is prepared from one or more of the following plants. The Old World balm of Gilead, or Mecca Balsam, is a small evergreen tree native to Asia and Africa. The American balm of Gilead is a species of poplar, populus candicans of the willow family. Also, balsam poplar varieties may also be use as well as the Cedronella canariensis variety from the Canary Island and the United States. The balm of Gilead is preferably used in liquid form rather than in its bulbous form. The balm of Gilead gives the soap composition therapeutic healing properties. The balm of Gilead helps disinfect the skin, act as a stringent, treat eczyma and other skin disorders, and relieve dry, scaly and itchy skin.

In addition, the present invention comprises aloe vera, which may be used in powder, juice or gel form. The aloe vera is preferably prepared from the whole leaf of the plant. Juice preparations are preferred, and gel forms are the more preferred embodiments. The aloe vera provides natural vitamins, minerals, enzymes, minerals, sugars, and other beneficial natural ingredients. The aloe vera opens up the pores of the skin, helps repair damaged skin tissues, moisturizes and hydrates the skin, rejuvenates the skin, and helps reduce and prevent skin blemishes and wounds.

The soap composition of the present invention also comprises all natural vitamins, minerals and amino acids. Preferably, an all-in-one powder multivitamin is used. Furthermore, beneficial mineral are provided preferably in low dosage. Finally, natural amino acids are also included to further help nourish the skin.

The present invention further comprises olive oil. Preferably, all-natural, 100% olive oil is used. Olive oil functions as an emollient and is useful in treating skin ailments such as psoriasis, excema and dermatitis treatment. It also helps keep the skin hydrated and functions as a lotion. It relieves dry skin and reduce scaling and inflammation.

Optional ingredients for the inventive composition include, among others, lavender, rosemary and other herbs and fragrances, natural oils, rose absolute and other fragrances, plant extracts, water, emulsifiers, bactericides, humectins, colorants, chelating agents, anti-oxidants and foaming improvers.

Furthermore, the present invention also comprises a method of making the soap bar product of the present invention, wherein the first step involves mixing all of the ingredients, except the titanium dioxide and zinc oxide, with a glycerin soap base. The second step involves: first adding the titanium dioxide; and second adding the zinc oxide.

The present invention concerns a soap product formulated and processed to provide one or more of the following advantageous properties: sunscreen protection through normal use (washing with and rinsing) with the soap product of the present invention; a natural skin absorber that penetrates the skin to a deep level to enhance the skin; nutrients to feed and nourish the skin to create and maintain healthier skin with improved complexion and more abundant collagen; reduction of acne, aging spots, and freckles with consistent use; and a gentle soap product with no harsh additive or unnatural ingredients.

Furthermore, the present invention also concerns a soap composition with optimal proportions of various ingredients for optimizing-SPF rating of the soap. Although it is generally expected that higher amounts of zinc oxide and titanium oxide would lead to higher SPF ratings, it has been found that increasing the amount of zinc oxide and titanium dioxide does not necessarily maximize the sunscreen SPF factor for the soap product.

Preferably, the amount of zinc oxide is added in greater proportion than the amount of titanium dioxide. For optimal SPF efficacy, the two physical sunblock ingredients, zinc oxide and titanium dioxide, are added in following proportions:

approximately 2 portions by weight of zinc oxide; to
approximately 1 portion by weight of titanium dioxide.

In one preferred embodiment, in preparing a 1.36 kg preparation of the present invention, approximately 7 g of zinc oxide is added, and approximately 3 g to 4 g of titanium dioxide is added.

Alternatively, approximately 0.4 % to 0.6 % by weight of the soap composition is preferably zinc oxide, and approximately 0.15 % to 0.3 % by weight of the soap composition is preferably titanium dioxide. Most preferably, approximately 0.5 % by weight of the soap is zinc oxide, and approximately 0.2 % by weight of the soap is titanium dioxide.

Furthermore, in one embodiment, in making a 1.36 kg preparation of the present invention, the following additional ingredients are added in the following proportions to optimize SPF ratings:

approximately 5 ml of balm of Gilead
approximately 10 ml of chlorophyll
approximately 8 g of multivitamin mixture
approximately 5 ml of olive oil
approximately 5 ml of aloe vera
approximately 15 ml of lemon juice.

Deviation from these proportions will continue to provide sunscreen protection. However, the soap composition of the present invention with these proportions are preferred.

Some of the preferred embodiments of the present invention are discussed below. As the present invention may be embodied in several forms without departing from the spirit or essential characteristics thereof, it should also be understood that the description contained herein is not limited by the details of the foregoing description, unless otherwise stated. The present invention should be construed within its spirit and scope, and therefore all changes and modifications that fall within the meets and bounds of the claims, or equivalences of such meets and bounds are therefore intended to be embraced by the invention.

The embodiment described below refers to approximate ranges of amounts of individual ingredients used to make approximately 1.36 kg (3 lb.) preparation of the soap of the present invention. Larger and small preparations may be made as known in the art.

DETAILED DESCRIPTION

The present invention concerns a soap base product that comprises physical UV protectants titanium dioxide and zinc oxide, wherein the UV protectants are applied to the skin by using the soap during normal wash. The soap composition of the present invention further comprises a soap base, chlorophyll, alpha-hydroxy acids (preferably citric acids), the healing balm of Gilead, aloe vera, multivitamins, minerals, olive oil and amino acids.

The present invention also optionally comprises ingredients, among others, lavender, rosemary and other herbs and fragrances, and other natural oils, rose absolute and other fragrances, plant extracts, water, emulsifiers, bactericides, humectins, colorants, chelating agents, anti-oxidants and foaming improvers.

Titanium Dioxide and Zinc Oxide

The present invention comprises two sunblock ingredients, titanium dioxide ($TiO_2$) and zinc oxide (ZO). Titanium dioxide and zinc oxide are well known physical UV blocking pigments. Titanium dioxide and zinc oxide are both very gentle on the skin. Zinc oxide, for example, is often used to treat diaper rash in infants and is a known therapeutic agent for the skin.

Physical sunblocks such as titanium dioxide and zinc oxide differ from chemical sunscreens in that they are not absorbed by the skin, but rather lie on top of the skin and prevent the UV rays from reaching the skin.

Microfine or ultrafine forms of titanium dioxide and zinc oxide are preferably used in the present invention. For the Titanium dioxide, a micronized version (microfine or ultrafine) is preferably used. Whereas pigmentary titanium dioxide is about 200 nm in size, ultrafine titanium dioxide is approximately 20 nm in size. These small particles are transparent and do not leave a visible residue. A micronized version of the $TiO_2$ is clear and provide equal amount of sunblocking capability.

$TiO_2$ is commercially available from various manufacturers. One suitable vendor is Kemira. $TiO_2$ from Kemira, UV-TITAN, is ultrafine transparent titanium dioxide, which increases protection against ultraviolet radiation and gives special effects in combination with metallic pigments. Kemira's titanium dioxide contains needle and spherical shaped crystals.

For ZnO, a micronized (ultrafine, microfine or nanospheric) version is also preferably used. More preferably, ZnO is in nanospheric form. The smaller particle size of the nanospheric form allows for better dispersion and interaction of ZnO with the other ingredients. Microfine zinc oxide provides stable and effective protection against ultraviolet radiation. Zinc oxide provides protection against UVB and UVA uniformly protecting from 290 to 380 nm. ZnO does not react with organic sunscreens when irradiated. Additionally, Zinc Oxide also gives the soap composition of the present invention anti-inflammatory qualities and helps calm irritated skin. Furthermore, ZnO also renders the inventive composition a skin protectant and wound healing adjuvant. Because ZnO is not absorbed into the body, it can safely be used with causing side effects.

ZnO from various manufacturers may be used. NanoActive™ Zinc Oxide form NanoScale Material, ultrafine and cosmetic grade (formula weight 81.37, catalog number 10-100), is one example. In other embodiments, Z-COTE®, which is a microfine ZnO, may also be used. Zinc oxide and the titanium dioxide are preferably paired, blended, or mixed together.

For a 1.36 kg preparation of the present invention, zinc oxide is added preferably at approximately between 2 g and 20 g, more preferably between approximately 3 and 10 g, and even more preferably between 6 and 8 g. Most preferably, approximately 7 g of zinc oxide is added.

For a 1.36 kg preparation of the present invention, between approximately 1 and 14 g of titanium dioxide is preferably added. More preferably, between approximately 2 and 5 g of titanium dioxide is added. Most preferably, approximately 2.5 to 3.5 g of titanium dioxide is added.

Chlorophyll

Chlorophyll is another active ingredient in the present invention, which provides therapeutic characteristics to the soap bar. The chlorophyll molecule is chemically similar to hemoglobin, the oxygen carrying element of human blood, except that chlorophyll's central atom is magnesium instead of iron. Preferably, the chlorophyll used in the present invention does not have any additives or preservatives. Chlorophyll can be added in liquid or powder form, more preferably in liquid form.

As an active ingredient in the present invention, chlorophyll promotes skin restoration and provides skin therapy. For example, chlorophyll helps the soap product of the present invention treat ulcerative lesions and burns. Chlorophyll also helps sooth burned and sunburned skin and provides pain relief, acting as a skin refresher.

Chlorophyll allows the present inventive compound to accelerate wound healing and stimulate damaged tissue repair. Chlorophyll also helps inhibit the growth of bacteria and therefore helps the soap composition function as a bacterio-static agent. Chlorophyll helps the soap composition provide an environment that interferes with bacterial growth. It also helps stimulate the growth of healthy granuloma tissue and fibroblasts. Furthermore, chlorophyll also helps the soap composition detoxify and deodorize. Thus, chlorophyll promotes wound healing, detoxifies and deodorizes, and inhibits bacterial growth.

In making a 1.36 kg preparation of the present invention, chlorophyll is preferably added at approximately between 5 and 20 ml, and more preferably at approximately between 7 ml and 15 ml. Most preferably, chlorophyll is added at approximately 10 ml.

Chlorophyll can be obtained from various manufacturers, including Nature's Sunshine. Chlorophyll by Nature's Sunshine contains photosynthetic chlorophyll and is made from alfafa. Any suitable source may be used for making chlorophyll as known in the art.

Citric Acid

The present invention further comprises an alpha-hydroxy acid. Preferably citric acid and more preferably lemon juice may be used. Alpha-hydroxy acids dissolve the cement that holds dead skin cells together and influences the structure of new stratum corneum being made. When citric acids is added at low concentration, it allows the soap composition to act as a mild exfoliant.

It also helps the skin absorb the other ingredients of the present invention by removing dead outer layers of the skin. Citric acid also helps the skin in its natural regenerating process by fading age spots and making the skin more flexible and smoother. Also functioning as skin moisturizers, the citric acid improves the overall tone of the skin and reduces lines and wrinkles.

In making a 1.36 kg preparation of the present invention, lemon juice is preferably added at amounts of approximately between 5 and 25 ml, and more preferably between approximately 10 and 20 ml. Most preferably, citric acid is added at approximately 15 ml.

Healing Balm of Gilead

The soap bar composition of the present invention further comprises the healing balm of Gilead. The balm of Gilead salve is made from one or more of the following balms of Gilead: Old World balm of Gilead, Canary Island balm of Gilead or the American balm of Gilead. Preferably, the balm is prepared from resinous juice of these plants.

Preferably, the historic Old World balm of Gilead, or Mecca balsam, is a small evergreen tree (*Commiphora gileadensis* or *C. opobalsamum*) of the family Burseraceae (incense-tree family), which is native to Africa and Asia and a common source of the commercial balm of Gilead. The American balm of Gilead is preferably a species of poplar tree (*Populus candicans*) of the family Salicaceae (willow family) which has large balsamic and fragrant buds. The poplar is closely related to, and sometimes considered a variety of, the balsam poplar (*P. tacamahaca, P. Nigra* and *P. balsamifera*), which has also been called balm of Gilead and tacamahac. The balm of Gilead may preferably also include the balsam fir and for herbaceous aromatic, shrubby plant (*Dracocephalum canariense* or *Cedronella canariensis*) of the family Labiatae (mint family) native to the Canary Islands and cultivated in parts of the United States. Also Abies Balsamea, Balm of Gilead Fir, or American Silver Fir, are names applied to Canadian species. Descriptions of the balm of Gilead from bontanical.com and encyclopedia.com are incorporated herein by reference.

Some additional synonyms of balm of Gilead include, among others: Balsamum Meccae var. Judiacum; Balsamum Gileadense; Baume de la Mecque; Balsamodendrum Opobalsamum; Balessan; Bechan; Balsam Tree; Amyris Gileadensis; Amyris Opobalsamum; Balsumodendron Gileadensis; Protium Gileadense; and Dosségmo.

The balm of Gilead provides therapeutic properties to the soap bar composition of the present invention. It helps disinfect the skin and act as an astringent. It also helps improve and prevent eczyma and other dry skin disorders. The balm of Gilead also provides treatments for skin infections, pimples, swellings, blemishes and other skin diseases. It also moisturizes and soothes the skin. Additionally, the balms referred to above pair well with the soap base, glycerin, providing the right texture to maximize sunscreen protection and penetration of the skin.

The balm of Gilead may be purchased from various commercial sources. One example is the balm of Gilead manufactured by Desert Herbals, *Populus Candicans*. Preferably, the balm of Gilead is added in liquid form. Powdered forms may be used. More preferably, the resinous liquid collected from the buds of the plants is used. Preferably, the balm of liquid used in the present invention is not processed from a different oil or wax.

Specifically, in a preferred embodiment, the balm of Gilead is derived from *Populus Candicans*. In another preferred embodiment, the balm of Gilead used is *P. Nigera*. In another preferred embodiment, the source is *P. Balsamifera*.

For a 1.36 kg preparation of the present invention, approximately 2 to 40 ml of balm of Gilead may be added. More preferably, between approximately 5 to 20 ml may be added. Most preferably approximately 5 ml of balm of gilead is added to a 1.36 kg preparation of the present invention.

Aloe Vera

The present invention further comprises aloe vera, which may be in liquid, gel or powder form. Liquid or gel forms are preferred. The aloe vera ingredient is preferably prepared using the whole leaf. Aloe vera, available commercially from various sources, may be used, and preferably the aloe vera should be prepared without additives or preservatives.

For a 1.36 kg preparation of the present invention, approximately 5 to 45 ml of aloe vera may preferably be added, and more preferably, 10 to 30 ml of aloe vera may be added. Most preferably, approximately 15 ml of aloe vera is added for a 1.36 kg preparation of the present invention.

Aloe vera itself comprises various components that are beneficial and therapeutic for the skin. (See positivehealth.com). Aloe vera contains vitamins, especially vitamin D and antioxidants vitamin A (beta-carotene), C and E and even traces of vitamin B 12. Aloe vera also contains small amounts of minerals such as calcium, sodium, potassium, manganese, magnesium, copper, zinc, chromium and selenium. As discussed in more detail below, these essential vitamins and minerals are delivered to the skin through the soap bar of the present invention. Additionally, beneficial enzymes such as bradykinase in the aloe vera help reduce inflammation of the skin when applied topically through the soap bar of the present invention.

Moreover, sugars in the aloe vera function as moisturizers and help detoxify the skin. Anthraquinones, which are phenolic compounds found in aloe vera, also enhance the soap bar's anti-bacterial and anti-viral properties. Additionally, lignins better allow the aloe vera to be absorbed into the skin. Saponins, which are soapy substances, have cleansing and antiseptic properties and function as anti-microbial, anti-bacterial, anti-viral, anti-fungal, and anti-yeast agents. Furthermore, small amounts of fatty acids present in aloe vera further give the soap composition anti-inflammatory characteristics. Salicyclic acid, which is also present in aloe vera, acts as anti-inflammatory and anti-bacterial agents. Finally, aloe vera contains 20 out of 22 amino acids, and 7 out of 8 amino acids, which cannot be synthesized by the body.

Aloe vera allows the present composition to work on damaged skin tissues and cells. It helps the soap composition heal burns, reduce eczema, and relieve skin irritations. Repeated use helps heal skin ulcers, prevents scarring, and rejuvenates the skin. Furthermore, it helps the soap moisture and hydrate the skin and leads to a softer and smoother skin. The aloe vera is absorbed into the skin to stimulate fibroblast replication and increases production of collagen and estain fibers. Importantly, aloe vera is hypo-allergenic and is generally safe for topical application.

Multivitamin, Minerals, and Amino Acids

Additional ingredients of the soap bar composition comprise vitamins, minerals, and amino acids. Preferably, these ingredients are added in powder form, but may also be added in liquid form. For a 1.36 kg preparation of the soap composition, approximately 4 to 16 g of a mixture of vitamins, minerals, and amino acids are added. More preferably approximately 8 g of a mixture of vitamins, mineral and amino acids are added to a 1.36 kg preparation of the present invention. Preferably, an all purpose multi-ingredient formulation may be used.

Although the vitamin should preferably include A, C, D, E, K, B1, B2, Niacin, B6, B12, folic acid, biotin, and others, one or more of these vitamins may also be missing. The vitamins in the soap composition provide added skin nutrition, replenish the skin with lost vitamins, reduce environmental effects on the skin, and help reverse signs of skin aging.

The soap composition of the present invention also comprises one or more minerals, such as Ca, Fe, P, Mg, Zn, Se, Cu, among others. Furthermore, natural amino acids are also added to the soap composition. Although naturally made amino acids are preferred, synthetic amino acids may also be used.

Soap Base

Glycerin is the preferred soap base in making the soap composition of the present invention. Glycerin acts as a natural humectant. Glycerin is hypo-allergenic and safe for use on sensitive skin. Other hypo-allergenic soap bases may also be used as known in the art. The soap base may comprise, for example, approximately 15-20 % pure glycerin, to which may be added approximately 7-13% additional lipids.

Preferably, vegetable or plant derived soap bases are chosen. Olive oil or coconut oil bases may also be used. Hemp oil and animal milk may also serve as the soap base. Lye derived soap bases, however, are preferably not used.

Optional Ingredients

Optionally, the soap composition of the present invention may also comprise one or more of the ingredients such as herbs or fragrance, oils or fats, plant extracts, water, emulsifiers, bactericides or anti-viral or anti-fungal agents, humectants, colorants, anti-oxidants, foaming improvers, and more. As known in the art, care should be taken to not add allergic ingredients. Additional ingredients to facilitate the soap function may also be incorporated as known in the art.

Method of Making

In making the soap composition of the present invention, the first step comprises mixing all of the ingredients (minus TiO2 & Zinc) in a professional quality glycerin soap base. Various commercially available soap making kits may be used. In the second step, first, TiO2 is added to the soap mixture, and then second, zinc oxide is added.

Preferred Proportions of Ingredients for Optimizing SPF Rating

Furthermore, the present invention also concerns a soap composition with optimal proportions of various ingredients for optimizing SPF rating of the soap. Preferably, the amount of zinc oxide is added in greater proportion than the amount of titanium dioxide.

For optimal SPF efficacy, the two physical sunblock ingredients, zinc oxide and titanium dioxide, were used with the following proportions:

approximately 2 portions by weight of zinc oxide; to approximately 1 portion by weight of titanium dioxide In a 1.36 kg preparation, preferably, approximately 6-8 g of ZnO and approximately 4-5 g of titanium dioxide is added.

Furthermore, in making a 1.36 kg preparation of the present invention, the following additional ingredients are added in the following proportions to optimize SPF ratings:
approximately 5 ml of balm of Gilead
approximately 10 ml of chlorophyll
approximately 8 g of multivitamin mixture
approximately 5 ml of olive oil
approximately 5 ml of aloe vera
approximately 15 ml of lemon juice.

Testing results also showed that an overall increase in the amount of sunblocks, titanium dioxide and zinc oxide, does not necessarily increase the SPF rating and may actually decrease the SPF rating in some examples.

Experimental Results

Experiments results are shown below for two different batches of soap compositions of the present invention.

In Batch No. 1, the various ingredients maintained the optimal SPF proportions discussed above. Thus, in Batch No. 1, zinc oxide and titanium dioxide maintained a 2 to 1 proportionality, respectively. For example, in making a 1.36 kg sample of the present invention, approximately 7 g of zinc oxide was added and approximately 3.5 g of titanium dioxide was added. Furthermore, the balm of Gilead, chlorophyll, multivitamins, olive oil, aloe vera, and lemon juice were added in proportions discussed above.

In Batch No. 2, however, with all other ingredients remaining the same, more titanium dioxide was added than zinc oxide. For a 1.36 kg preparation, approximately 10 g of zinc oxide was added and approximately 20 g of zinc oxide was added.

As shown below, experimental results showed that Batch No. 1 showed a higher SPF protection. The results show that a 2:1 ratio between zinc oxide and titanium dioxide provides optimal SPF rating. The results show that it is desirable to have more zinc oxide than titanium dioxide. Furthermore, even though Batch No. 2 had more sunblock ingredients, Batch No. 1 unexpectedly showed better SPF rating.

Experimental Procedure and Results

SPF determination of the sunscreen soap was conducted by AMA Laboratories utilizing a modification of the Final Monograph procedure; "Sunscreen Drug Products for Over-The-Counter Human Use," Final Rule, 21 CFR Part 352, Subpart D (Federal Register/Vol. 64, No. 98/Friday May 21, 1999).

These Batches were each subjected to two different tests. The first test, "Not In Use" test, generally dissolved the soap compositions in a 50% solution and applied it to human skin subjects at a dose of 4 mg/cm². After allowing the solution to dry for 15 minutes, UV exposure testings were conducted. A second test, "In Use" test, generally directed human subjects to lather and rinse their skins with the soap compositions in a manner normally associated with typical washing with a bar soap product. Their skins were then exposed to UV rays from the solar simulator.

Also, the samples submitted to AMA Labs for both Feb 7 tests were the same (called Sunsoap Batch 1 in the reports) and the samples tested for the May 24/25 tests were the same (called Sunscreen Soap 2 in the reports).

Test 1: Batch No. 1, "Not In Use" Test

Objective: The subject were convened to evaluate the effectiveness of a test material as a sunscreen product by determining the static Sun Protection Factor (SPF) on human skin using a modification of the procedure as defined by the Final Monograph; "Sunscreen Drug Products Fr Over-The-Counter Human Use", Final Rule, 21 CFR Part 352, Subpart D (Federal Register/Vol. 64, No. 98/Friday May 21, 1999, Proposed Amendment; Docket number 78N-0035/CP12, Jun. 21, 1999).

Batch No. 1: Batch No. 1, labeled Sunsoap Batch 1, was received and assigned AMA Lab No.: K-7285. Upon arrival at AMA Laboratories, Inc., the test material was assigned a unique laboratory code number and entered into a daily log identifying the lot number, sample description, sponsor, date received and testes requested.

Five subjects were tested. The subjects' ages ranged between 23 and 59. They were female Caucasians. Standards of inclusion in the study were, among others: individuals eighteen years of age or older; individuals free of any dermatological or systemic disorder which would interfere with the results; individuals free of any acute or chronic disease that might interfere with or increase the risk of study participation; individuals with Fitzpatricks skin type 1, II, and II only; individual with no uneven skin tones, pigmentation, scars, other irregularities or hair in test site areas that would interfere with SPF determination; individual who will complete a preliminary medical history form mandated by AMA Laboratories, Inc. and are in general good health; individuals able to cooperate with the Investigator and research staff, be willing to have test materials applied according to the protocol, and complete the full course of the study; individuals willing to refrain from using any sunscreen products, sunbathing or tanning bed use 24 hours prior to study initiation and the entire duration of the study; and individuals with excessive hair on their back who are willing to clip or shave their hair.

Standards of exclusion from the study were: individuals who are under a doctor's care; individuals who are currently taking any medication (topical or systemic) that may mask or interfere with the test results; subjects with a history of any form of skin cancer, melanoma, lupus, psoriasis, connective tissue disease, diabetes or any disease that would increase the risk associated with study participation; individuals diagnosed with chronic skin allergies; individuals with a history of adverse effects upon sun exposure; female volunteers who indicate that they are pregnant or lactating; individuals with blemishes, nevi, sunburn, suntan, scars, moles, active dermal lesions or uneven pigmentation in the test sites; and individuals with known hypersensitivity to any sunscreen products.

Healthy volunteers over the age of 18 years were recruited for this study. The subjects consisted of fair-skin individuals with skin types I, II, or III defined as follows (Federal Register Vol. 64, No. 98, 27690, 1999) (Based on the first 30 to 45 minutes sun exposure after a inter season of no sun exposure): Type I—Always burns easily and never tans; Type II—Always burns easily and tans minimally; Type III—Burns moderately and tans gradually.

Institutional Review Board: A trained technician performed a physical examination of the subjects' back to determine if study eligibility criteria were satisfied. The Institutional Review Board followed reference, CTR Title 21 Part 56, Subparts A, B, C, and D. The IRB of AMA Laboratories, Inc. consisting of five or more individuals, chosen from within the company for technical expertise and from local community for lay interaction.

Artificial Light Source: The light source employed was a 150 watt Xenon Arc Solar Simulator (Solar Light Co., Philadelphia, Pa. Model 14S or Model 16S) having a continuous emission spectrum in the UVB range from 290 to 320 nm. Xenon arc is selected on the basis of its black body radiation temperature of 6000° K which produces continuous UV spectra (all wavelengths) substantially equivalent to that of a natural sunlight (Berger, D.S.: Specification and Design of Solar Ultraviolet Simulators, J. Invest, Dermatol. 53: 192-199, 1969).

The device was equipped with a dichroic mirror (which reflects all radiation below 400 nm) and works in conjunction with a 1mm thick Schott Wg-320 filter (which absorbs all radiation below 290 nm) to produce simulation of the solar UVA-UVB spectrum. A 1 mm thick UG 11 filter (black lens) was added to remove reflected (infra-red, grater than 700 nm) heat and remained visible radiation. UVB radiation was monitored continuously during exposure using a Model DCS-1 Sunburn UV Meter/Dose Controller System (Solar Light Co.) formerly known as the Robertson-Berger Sunburn Meter (R-B meter). Measurements were taken at a position within 8 mm from the surface of the skin. The field of irradiation was 1 cm in diameter. The solar simulator was allowed a warm up time of at least 15 minutes before use and power supply output was recorded.

Procedure: (Static SPF Determination Including 8% Homosalate Standard)

The infrascapular area of the back to the right and left side of the midline was used. Within this area, 50 $cm_2$ rectangular test sites were delineated with a gentian violet surgical skin marker. Sites were observed to ensure uniform pigmentation, skin tone and texture, and absence of warts, moles, nevi, scars, blemishes and active dermal lesions. Any areas that might be expected to produce erratic results were not used for UV exposures.

The procedure for this study is outlined in the Federal Register/Vol. 64, No. 98/Friday May 21, 1999. One test site area served to determine each subject's Minimal Erythema Dose (MED). A minimum of five UV exposures was administered within this site. The individuals subject MED is the shortest time of exposure that produces minimally perceptible erythema at 22 to 24 hours post irradiation.

The test material, 8% homosalate standard were shaken and/or swirled with a glass rod before use and were evenly applied using plastic volumetric syringes to rectangular areas measuring 5 cm×10 cm (50 $cm^2$) for a final concentration of 2.0 mg/cm 2. Evenness of application was verified by observation with a Woods Lamp.

Fifteen minutes after application, a protected site received a series of seven UV exposures based upon previously determined MED. All immediate responses were recorded after UV radiation exposure from the solar simulator.

The UV exposures for test material, 8% homosalate standard were calculated from previously determined MED and the intended SPF as follows. SPF 4: MED times 0.64x, 0.80x, 0.90x. 1.00x, 1.10x, 1.25x, and 1.56x. SPF 15: MED times 0.69x, 0.83x, 0.91x, 1.00x, 1.09x, 1.20x and 1.44x, where x equals the expected SPF of the product.

Deviation From Protocol: Prior to application of the test sample (AMA Lab No.: K-7285), it was allowed to dissolve in water, such that it was diluted to a concentration of 50%. The prepared solution was then delivered to the site at a dosage of 4.0 mg/$cm^2$.

Fifteen minutes following the application procedure, the protected site received a series of seven UV exposures based upon previously determined MED.

Evaluation of Responses: Twenty-two to twenty-four hours post exposure, the subjects are instructed to return to the testing facility for evaluation of delayed erythemic responses. The technician who evaluates the MED did not know the identity of the test product application sites and UV exposures. Also he/she was not the same person to have applied the sunscreen product to the test site or administered the doses of UV radiation.

SPF=Protected MED/Final unprotected MED.

Visual Grading Scale:
   0=No Erythema
   ?=Questionable Erythema
   1=Minimal Erythema
   2=Slight Erythema
   3=Well-Defined Erythema
   4=Erythema and Edema
   5=Erythema and Edema in vesicles All technical employees of AMA Laboratories, Inc. were required to take and pass a visual discrimination examination conducted by a Board Certified Ophthalmologist using the Farnsworth-Munsell 100 Hue Test as published; which determines a person's ability to discern color against a black background. This test was additionally modified to include a flesh tone background more nearly approaching actual use conditions, wherein erythematous skin is graded according to intensity.

Determination of the Test Products SPF Value and PCD/Calculation of SPF and PCD: The mean SPF value (x) was calculated using a minimum of 20 evaluable subjects per formulation. The standard deviation was determined (s). The upper 5% point was obtained from the t distribution table with n-1 degrees of freedom (t). First, A was calculated as follows:

$A=(t)(s)/\sqrt(n)$

Therefore, the label SPF for panels using a minimum of 20 evaluable subjects was the largest whole number less the mean SPF minus A.

Label SPF=Mean SPF–$A$.

The Product Category Designation (PCD), for labeling purposes, was assigned based on the mean SPF and PCD ranking according to the reference. Classifications may be High, Moderate, or Minimal. Because only five test panelists were included in this study, no PCD was assigned.

Rejection Criteria: Panelist's results were rejected and the panelist replaced if: 1) An exposure series fails to elicit and MED response on the untreated skin, and the test is considered a technical failure even if the MED response is observed in the protected site; 2) The responses on the protected are randomly absent, indicating uneven product spreading, non-constant light irradiance or unstable product; and 3) All exposures in a series of elicit responses—thus prohibiting any MED calculation.

Observations: No adverse effects or unexpected reactions of any kind were observed on any of the subjects.

Results: The SPF of the above test material when tested on five subjects as described herein under static, in-use, conditions yielded the mean SPF of 13.95. The mean SPF of the 8% homosalate standard on the same panel was 4.24.

TABLE 1

(Batch No. 1 (Not In Use Test): Sunsoap Batch 1)

| Subject ID # | Sex | MED/ Hr | I (Amps) | Skin Type | MED I $J/M^2$ | MED II $J/M^2$ | STD (8% HMS) | SPF Value |
|---|---|---|---|---|---|---|---|---|
| 56 2392 | F | 125.8 | 7.0 | II | 46.20 | 46.20 | 4.00 | 13.65 |
| 36 0202 | F | 125.8 | 7.0 | II | 46.20 | 46.20 | 4.40 | 15.00 |

TABLE 1-continued (Batch No. 1 (Not In Use Test): Sunsoap Batch 1)

| Subject ID # | Sex | MED/ Hr | I (Amps) | Skin Type | MED I J/M² | MED II J/M² | STD (8% HMS) | SPF Value |
|---|---|---|---|---|---|---|---|---|
| 50 1415 | F | 125.8 | 7.0 | II | 46.20 | 46.20 | 4.40 | 15.00 |
| 40 1976 | F | 128.6 | 7.0 | II | 60.89 | 60.89 | 4.00 | 12.45 |
| 68 2925 | F | 125.9 | 7.0 | II | 46.20 | 46.20 | 4.40 | 13.65 |
| Mean (x) | | | | | | | 4.24 | 13.95 |
| Standard Dev (s) | | | | | | | 0.22 | 1.08 |
| Std. Error | | | | | | | 0.10 | 0.48 |
| S.E. % of Mean | | | | | | | 2.36 | 3.44 |
| N | | | | | | | 5 | 5 |

MED: Minimal Erythemal Dose
I: Intensity of Light Source

Test 2: Batch No. 1, "In Use" Test

In Test No. 2, Batch No. 1 (referred to as Sunsoap Batch 1 and assigned AMA Lab No.: K-7285) was conducted to an "In Use" Test. The subjects tested were again five people, ranging in age from 41 to 53, with 1 Caucasian male and 4 Caucasian females. No adverse effects or unexpected reactions of any kind were observed on any of the subjects.

The subjects underwent "In Use" tests, which directed the subjects to lather and rinse their forearms with the soap compositions in a manner normally associated with typical washing with a bar soap product. Their forearms were then exposed to UV rays from the solar simulator. Otherwise, same protocols were followed as in the previous test.

Results: The SPF of the above test material when tested on five subjects as described herein under static, in-use, conditions yielded the mean SPF of 4.68. The mean SPF of the 8% homosalate' standard on the same panel was 4.08.

TABLE 2

(Batch No. 1 (In Use Test): Sunsoap Batch 1)

| Subject ID # | Sex | MED/ Hr | I (Amps) | Skin Type | MED I J/M² | MED II J/M² | STD (8% HMS) | SPF Value |
|---|---|---|---|---|---|---|---|---|
| 64 7285 | F | 125.5 | 7.0 | II | 60.89 | 60.89 | 4.40 | 4.00 |
| 54 3471 | F | 127.0 | 7.1 | II | 60.89 | 60.89 | 4.00 | 5.00 |
| 46 0816 | F | 128.3 | 7.0 | II | 46.20 | 46.20 | 4.00 | 5.00 |
| 40 5027 | F | 126.3 | 7.0 | II | 46.20 | 46.20 | 4.00 | 5.00 |
| 48 5699 | M | 126.8 | 6.9 | II | 46.20 | 46.20 | 4.00 | 4.00 |
| Mean (x) | | | | | | | 4.08 | 4.687 |
| Standard Dev (s) | | | | | | | 0.18 | 0.46 |
| Std. Error | | | | | | | 0.08 | 0.21 |
| S.E. % of Mean | | | | | | | 1.96 | 4.49 |
| N | | | | | | | 5 | 5 |

MED: Minimal Erythemal Dose
I: Intensity of Light Source

Test 3: Batch No. 2, "Not In Use" Test

In Test No. 3, Batch No. 2 (referred to as Sunscreen Soap 2 and assigned AMA Lab No.: K-7598) was subjected to a "Not In Use" Test. The subjects tested were again five people, ranging in age from 20 to 53, who were all Caucasian females. No adverse effects or unexpected reactions of any kind were observed on any of the subjects.

A "Not In-Use" evaluation procedure was followed as in Test 1. Prior to application of the test sample, it was allowed to dissolve in water, such that it was diluted to a concentration of 50%. The prepared solution was then delivered to the site at a dosage of 4.0 mg/cm². Otherwise, same protocols were followed as in the previous tests.

Results: The SPF of the above test material when tested on five subjects as described herein under static, "In-Use" conditions yielded the mean SPF of 11.85. The mean SPF of the 8% homosalate standard on the same panel was 2.24.

TABLE 3

(Batch No. 2 (Not In Use Test): Sunscreen Soap 2)

| Subject ID # | Sex | MED/ Hr | I (Amps) | Skin Type | MED I J/M² | MED II J/M² | STD (8% HMS) | SPF Value |
|---|---|---|---|---|---|---|---|---|
| 64 7285 | F | 125.4 | 7.8 | II | 60.89 | 60.89 | 4.40 | 10.35 |
| 46 9012 | F | 128.1 | 7.8 | II | 46.20 | 46.20 | 4.00 | 13.65 |
| 40 8279 | F | 126.2 | 7.8 | II | 46.89 | 46.89 | 4.40 | 12.45 |
| 50 1415 | F | 127.6 | 7.7 | II | 46.20 | 60.89 | 4.00 | 12.45 |
| 58 3434 | F | 126.5 | 7.2 | II | 30.33 | 30.33 | 4.40 | 10.35 |
| Mean (x) | | | | | | | 4.24 | 11.85 |
| Standard Dev (s) | | | | | | | 0.22 | 1.45 |
| Std. Error | | | | | | | 0.10 | 0.65 |
| S.E. % of Mean | | | | | | | 2.36 | 5.49 |
| N | | | | | | | 5 | 5 |

MED: Minimal Erythemal Dose
I: Intensity of Light Source

Test 4: Batch No. 2, "In Use" Test

In Test No. 4, Batch No. 2 (referred to as Sunscreen Soap 2 and assigned AMA Lab No.: K-7598) was subjected to an "In Use" Test. The subjects tested were again five people, ranging in age from 20 to 53, who were all Caucasian females. No adverse effects or unexpected reactions of any kind were observed on any of the subjects.

An "In-Use" evaluation procedure was followed for this test, whereby study participants were instructed to lather the test material on the forearm test sites and rinse in a manner consistent with which they would typically was with a soap product. Their forearms were then exposed to UV rays from the solar simulator. Otherwise, same protocols were followed as in the previous tests.

Results: The SPF of the above test material when tested on five subjects as described herein under static, "In-Use" conditions yielded the mean SPF of 3.92. The mean SPF of the 8% homosalate standard on the same panel was 4.24.

TABLE 4

(Batch No. 1 (In Use Test): Sunscreen Soap 2)

| Subject ID # | Sex | MED/ Hr | I (Amps) | Skin Type | MED I J/M² | MED II J/M² | STD (8% HMS) | SPF Value |
|---|---|---|---|---|---|---|---|---|
| 64 7285 | F | 125.4 | 7.8 | II | 60.89 | 60.89 | 4.40 | 3.20 |
| 46 9012 | F | 128.1 | 7.8 | II | 46.20 | 46.20 | 4.00 | 4.00 |
| 40 8279 | F | 126.2 | 7.8 | II | 46.89 | 46.89 | 4.40 | 4.40 |
| 50 1415 | F | 127.6 | 7.7 | II | 46.20 | 60.89 | 4.00 | 4.00 |
| 58 3434 | F | 126.5 | 7.2 | II | 30.33 | 30.33 | 4.40 | 4.00 |
| Mean (x) | | | | | | | 4.24 | 3.92 |
| Standard Dev (s) | | | | | | | 0.22 | 0.44 |
| Std. Error | | | | | | | 0.10 | 0.20 |
| S.E. % of Mean | | | | | | | 2.36 | 5.10 |
| N | | | | | | | 5 | 5 |

MED: Minimal Erythemal Dose
I: Intensity of Light Source

I claim:

1. A cleansing composition in soap bar form for providing UV protection through normal use of washing and rinsing and for therapeutic and restorative properties, consisting of:
   a natural soap base for cleaning the skin;
   titanium dioxide and zinc oxide for providing protection against UV rays, wherein said zinc oxide and titanium dioxide are in 2:1 ratio and are in ultrafine or microfine form;
   chlorophyll for promoting wound healing, detoxifying, deodorizing, and inhibiting bacterial growth;
   lemon juice for providing a mild exfoliant to help remove dead skin cells and help skin regenerate;
   healing balm of Gilead prepared from one or more selected from the group consisting of Old World balm of Gilead, Canary Island balm of Gilead, and American or Canadian balm of Gilead;
   aloe vera prepared from whole leaf of aloe vera for restoring damaged skin tissues and cells;
   one or more vitamin selected from the group consisting of A, C, D, L, K, B 1, B2, Niacin, B6, B 12, folic acid, and biotin;
   olive oil for moisturizing and keeping skin hydrated;
   one or more minerals selected form the group consisting of Ca, Fe, P, Mg, Zn, Se, and Cu; and
   amino acids,
   wherein the cleansing composition is in soap bar form; and
   wherein balm of Gilead, chlorophyll, olive oil, aloe vera, and lemon juice are present in ratio of 1:2:1:1:3 proportions, respectively.

2. The cleansing composition according to claim 1, wherein the cleansing composition does not contain preservatives.

3. The cleansing composition according to claim 1, wherein the natural soap base is glycerin.

4. The cleansing composition according to claim 1, wherein the natural soap base is a plant derived soap base.

5. The cleansing composition according to claim 1, wherein the ultra-fine or micro-fine zinc oxide is nanospheric in form.

6. The cleansing composition according to claim 1, wherein the balm of Gilead is prepared from resinous juice.

7. The cleansing composition according to claim 1, wherein the vitamin is a multi-vitamin.

8. The cleaning composition according to claim 1, wherein the amino acids are naturally made amino acids.

9. A cleansing composition in soap bar form for providing UV protection through normal use of washing and rinsing and for therapeutic and restorative properties, consisting of:
   a natural soap base for cleaning the skin;
   titanium dioxide and zinc oxide for providing protection against UV rays, wherein said zinc oxide and titanium dioxide are in 2:1 ratio and are in ultrafine or microfine form;
   chlorophyll for promoting wound healing, detoxifying, deodorizing, and inhibiting bacterial growth;
   lemon juice for providing a mild exfoliant to help remove dead skin cells and help skin regenerate;
   healing balm of Gilead prepared from one or more selected from the group consisting of Old World balm of Gilead, Canary Island balm of Gilead, and American or Canadian balm of Gilead;
   aloe vera prepared from whole leaf of aloe vera for restoring damaged skin tissues and cells;
   one or more vitamin selected from the group consisting of A, C, D, L, K, B 1, B2, Niacin, B6, B12, folic acid, and biotin;
   olive oil for moisturizing and keeping skin hydrated;
   one or more mineral selected form the group consisting of Ca, Fe, P, Mg, Zn, Se, and Cu;
   amino acids; and
   one or more component selected from the group consisting of fragrance, oil, fat, water, bactericide, anti-viral agent, anti-fungal agent, colorants, anti-oxidants, and foaming improvers;
   wherein the cleansing composition is in soap bar form; and
   wherein balm of Gilead, chlorophyll, olive oil, aloe vera, and lemon juice are present in ratio of 1:2:1:1:3 proportions, respectively.

10. A method of providing sunscreen to the skin by washing and rinsing with a cleansing composition,
   wherein the cleansing composition is in soap bar form,
   wherein the cleansing composition provides therapeutic and restorative properties,
   wherein the soap composition consists of:
   a natural soap base for cleaning the skin;
   titanium dioxide and zinc oxide for providing protection against UV rays, wherein said zinc oxide and titanium dioxide are in 2:1 ratio and are in ultrafine or microfine form;
   chlorophyll for promoting wound healing, detoxifying, deodorizing, and inhibiting bacterial growth;
   lemon juice for providing a mild exfoliant to help remove dead skin cells and help skin regenerate;
   healing balm of Gilead prepared from one or more selected from the group consisting of Old World balm of Gilead, Canary Island balm of Gilead, and American or Canadian balm of Gilead;
   aloe vera prepared from whole leaf of aloe vera for restoring damaged skin tissues and cells;
   one or more vitamin selected from the group consisting of A, C, D, L, K, B 1, B2, Niacin, B6, B12, folic acid, and biotin;
   olive oil for moisturizing and keeping skin hydrated;
   one or more mineral selected form the group consisting of Ca, Fe, P, Mg, Zn, Se, and Cu; and
   amino acids;
   wherein balm of Gilead, chlorophyll, olive oil, aloe vera, and lemon juice are present in ratio of 1:2:1:1:3 proportions, respectively.

11. A method of making a soap bar composition for imparting UV protection on the skin by washing and rinsing with the cleansing composition consisting of,
   mixing the following ingredients in a soap base:
      chlorophyll for promoting wound healing, detoxifying, deodorizing, and inhibiting bacterial growth;
      lemon juice for providing a mild exfoliant to help remove dead skin cells and help skin regenerate;
      healing balm of Gilead prepared from one or more selected from the group consisting of Old World balm of Gilead, Canary Island balm of Gilead, and American or Canadian balm of Gilead;
      aloe vera prepared from whole leaf of aloe vera for restoring damaged skin tissues and cells;
      one or more vitamin selected from the group consisting of A, C, D, L, K, B1, B2, Niacin, B6, B12, folic acid, and biotin;
      olive oil for moisturizing and keeping skin hydrated;
      one or more mineral selected form the group consisting of Ca, Fe, P, Mg, Zn, Se, and Cu; and
      amino acids;
   adding titanium dioxide to the soap mixture;
   adding zinc oxide to the titanium dioxide, which are in 2:1 ratio, added soap mixture; and
   wherein balm of Gilead, chlorophyll, olive oil, aloe vera, and lemon juice are present in ratio of 1:2:1:1:3 proportions, respectively.

* * * * *